United States Patent [19]

Norgren et al.

[11] Patent Number: 4,596,036

[45] Date of Patent: Jun. 17, 1986

[54] METHOD AND APPARATUS FOR FRINGE-SCANNING CHROMOSOME ANALYSIS

[75] Inventors: Richard M. Norgren, Palo Alto; Joe W. Gray; Tomas B. Hirschfeld, both of Livermore, all of Calif.

[73] Assignee: The United States of America as represented by the United States Department of Energy, Washington, D.C.

[21] Appl. No.: 528,284

[22] Filed: Aug. 31, 1983

[51] Int. Cl.$^4$ .......................... G06K 9/00; G01N 15/02
[52] U.S. Cl. ........................................ 382/6; 356/336; 356/338; 377/10
[58] Field of Search ...................... 382/6, 31; 350/3.67, 350/3.68; 364/416; 377/10, 11; 356/335, 336, 337, 338, 339, 340, 341, 342, 343

[56] References Cited

U.S. PATENT DOCUMENTS

| | | | |
|---|---|---|---|
| 3,680,961 | 8/1972 | Rudd | 356/102 |
| 3,953,128 | 4/1976 | Holly | 356/106 R |
| 4,318,180 | 3/1982 | Lundquist et al. | 356/336 |
| 4,329,054 | 5/1982 | Bachalo | 356/336 |
| 4,338,024 | 7/1982 | Bolz et al. | 382/6 |
| 4,387,993 | 6/1983 | Adrian | 356/336 |
| 4,475,236 | 10/1984 | Hoffman | 382/6 |

OTHER PUBLICATIONS

Farmer, "Measurement of Particle Size, Number Density, and Velocity using a Laser Interferometer," *Applied Optics*, vol. 11, pp. 2603-2612 (1972).

Deutsch, *Estimation Theory*, Prentice-Hall, Inc., N.J. (1965).

Norgreen, et al., "Restoration of Profiles from Slit-Scan Flow Cytometry," *IEEE Transactions on Biomedical Engineering*, vol. BME-29, pp. 101-106 (1982).

Carrano, et al., "Flow Cytogenetics: A New Approach to Chromosome Analysis," *Flow Cytometry and Sorting*, Chapter 23, John Wiley and Sons, New York.

Gray, et al., "Slit-Scan Flow Cytometry of Mammalian Chromosomes," *J. Histochem. Cytochem.*, vol. 27, pp. 441-444 (1979).

Primary Examiner—Leo H. Boudreau
Attorney, Agent, or Firm—Stephen C. Macevicz; L. E. Carnahan; Judson R. Hightower

[57] ABSTRACT

Apparatus and method are provided for analyzing sub-micron-sized features of microscopic particles. Two central features of the invention are (1) constraining microscopic particles to flow with substantially constant orientation through a predetermined interference fringe pattern, and (2) estimating particle structure by analyzing its fringe profile. The invention allows nearly an order of magnitude higher resolution of chromosome structure than possible with currently available flow system techniques. The invention allows rapid and accurate flow karyotyping of chromosomes.

14 Claims, 6 Drawing Figures

METHOD AND APPARATUS FOR FRINGE-SCANNING CHROMOSOME ANALYSIS

BACKGROUND OF THE INVENTION

The U.S. Government has rights in this invention pursuant to Contract No. W-7405-ENG-48 between the U.S. Department of Energy and the University of California, for the operation of Lawrence Livermore National Laboratory.

This invention relates generally to morphological analysis of microscopic particles suspended in a fluid stream and, more particularly, to flow karyotyping of chromosomes.

As the major packaging unit of genetic material, chromosomes have broad relevance to basic and applied genetics, to clinical medicine, and to public health. Structural rearrangements of chromosomes and abnormalities in chromosome number cause major heritable disorders in man; for example, mongolism (Down's syndrome) is usually due to the occurrence of an extra chromosome 21, the cri du chat syndrome occurs from a partial deletion of chromosome 5, and the chronic myelogenous leukemia is associated primarily with a translocation between one chromosome 9 and one chromosome 22 (see also, Yunis, "The Chromsomal Basis of Human Neoplasia, " Science, vol. 221, pp. 227-236, for a discussion of the general relation between cancer and chromosomal defects, especially those correlated with anamolous chromosomal banding patterns). Mankind is also faced with the serious challenge of discovering and monitoring the genetic effects of an ever-increasing array of environmental factors that affect the integrity of chromosomes. The appearance of chromosomal abnormalities either in the cells of exposed individuals or in well-defined test systems provides a means for assaying genetic damage.

The traditional approach to the analysis of mitotic chromosomes involves (1) obtaining the cells by biopsy or cell culture; (2) fixing highly flattened cells to microscope slides; (3) staining to give high-contrast chromosomal images or to elicit chromosomal bands; (4) finding and photographing good metaphase chromosomes; and (5) "cutting and pasting" by a cytogeneticist to assemble homologous pairs of chromosomes according to karyotypic conventions. The method is painstaking, tedious, slow, expensive, and subjective; it is ill-suited to population monitoring and to large-scale screening for clastogens (agents that break chromosomes).

Over the past decade, much effort has been devoted to the development of comprehensive chromosome analyzers intended to replace the cytogeneticist in the analysis of metaphase chromosomes. In particular, flow cytometers have been employed to generate chromosomal DNA (deoxyribonucleic acid) distributions which yield relative chromosomal DNA content and frequency for the identification of chromosomes of a species or a cell population (see Melamed, et al., Flow Cytometry and Sorting, John Wiley and Sons, New York, for a general review of flow cytometry technology, including a description of its use for flow karyotyping). As long as the chromosomes of a species or cell population are each sufficiently different in size (or more particularly, each sufficiently different in DNA content), they can be separately identified in the DNA content-versus-frequency data. Such measurements are suitable for detecting certain homogeneous chromosome abnormalities that are the same in many cells or every cell of a population, such as aneuploidy, chromosomal deletions involving the loss of a chromosome segment, and translocations involving the transfer of a chromosome segment from one chromosome to another.

There are two major drawbacks to karyotyping on the basis of DNA content alone. First, different chromosomes frequently have indistinguishable DNA content. Therefore, not all of the chromosomes are uniquely resolved. And second, many chromosomal aberrancies, such as translocations may not be associated with significant losses or gains of DNA, thus cannot be distinguished from normal chromosomes. To overcome these drawbacks, effort has been directed to developing flow cytometers which can determine the distribution of DNA along individual chromosomes. This capability allows measurement of the centromeric index and length of chromosomes as well as total DNA content. (Centromeres are regions along the chromosome of relatively low DNA content which are involved in the chromosome-separation process during mitosis. The centromeric index, the relative position of the centromere along the chromosome, is a basic descriptor of chromosome structure.) The first attempt in this direction was the slit-scan flow cytometer (Gray, et al., "Slit-Scan Flow Cytometry of Mammalain Chromosomes, J. Histochem. Cytochem., Vol. 27, pp. 441–444 (1979)). In this device, chromosomes are constrained to flow through a laser beam whose profile at the point of intersection forms a narrow ellipse. In addition, a narrow slit is provided through which fluorescence is collected. The chromosomes flow longitudinally through the narrow dimension of the laser beam so that the beam sweeps along the length of the chromosome exciting attached fluorescent dyes. The slit limits the region along the chromosome over which fluorescence is collected, thereby allowing further resolution of the distribution of DNA along the chromosome. The theoretical resolving power of such a device depends on how narrowly the excitation beam can be focused down. Beam widths down to 0.25 $\mu$m are obtainable; however, as the beam width is narrowed the depth of focus becomes correspondingly smaller (for small beam widths the magnitude of the depth of focus is about the same as the beam width itself). As the beam width (and hence depth of focus) becomes smaller, greater numbers of particles pass through the beam out of focus; thus particles passing through the beam are not illuminated by uniformly intense light. Beam widths corresponding to practical depths of focus limit resolution to about 2-3 $\mu$m.

Quite apart from chromosome analysis, an industrial technology has been developed for measuring the sizes, densities, and velocities of small particles, such as spray droplets, bubbles, filaments and the like. Laser anemometers and laser Doppler velocimeters are part of this technology. These devices comprise convergent laser beams of substantially equal size, intensity and frequency which produce either a stationary or a moving interference fringe pattern within the zone of convergence. Roughly the interference fringes are a series of parallel "slabs" of high light intensity separated by regions of little or no light intensity. The intensity profile along a line perpendicular to the "slabs" appears as an equi-spaced series of sine-squared curves whose amplitude maxima define a Gausian curve, referred to as the "envelope" of the series. The maximum of the envelope Gausian corresponds approximately to the center "slab" of the series. The spacing between the "slabs" of light, or fringes, and their widths depend on the angle of intersection of the convergent laser beams and wavelength. The spacing between the fringes (e.g., the distance between successive maxima of the sine-squared curves) will be referred to as the interfringe distance. Provided that a particle's size is less than or approximately equal to the interfringe distance, its velocity is readily determined as it passes across the set of fringes. During transit, the particle scatters light successively from each of the fringes. Velocity is determined by recording the time between successive "peaks" of scattered light and by knowledge of the interfringe distance. As recognized by the art (e.g., Farmer, "Measurement of Particle Size, Number Density, and Velocity Using a Laser Interferometer", *Applied Optics*, Vol. 11, pp. 2603-2612 (1972)) particle size can be estimated when the interfringe distance is comparable to particle diameter. A range of sizes can be detected by observing the amplitude of intensity oscillations in the scattered light signal as particles pass through the fringe set. The amplitude is greatest for particles whose sizes are comparable to the interfringe distance; the amplitude decreases as particle size approaches the size of the fringe set.

The foregoing illustrates the limitations of the current technology. It is apparent that it would be advantageous to provide an alternative to available methods, particularly in regards to determining the morphology of structure of microscopic particles.

SUMMARY OF THE INVENTION

It is, therefore, an object of the invention to provide a method and apparatus for determining the morphology or structure of microscopic particles suspended in a fluid.

Another object of the invention is to provide a method and apparatus for determining the distribution of fluorescent labels on microscopic biological particles, such as cells, chromosomes, or the like.

Still another object of the invention is to provide a rapid and automated means for karyotyping chromosomes, particularly mammalian chromosomes.

Another object of the invention is to provide a method and apparatus for determining individual and population averages of sub-micron-sized structural features of microscopic particles.

A further object of the invention is to provide a rapid and automated means for detecting and quantifying chromosomal aberrancies such as aneuploidy, polycentrics, chromosomal breaks, translocations, and the like.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

These and other objects are attained in accordance with the present invention wherein, generally, microscopic particles suspended in a fluid are constrained to flow along the same substantially linear path, where they are sequentially illuminated by one or more sets of interference fringes. Below, the fluid containing the suspension of microscopic particles is referred to as the carrier fluid, and the same substantially linear path along which the particles flow is referred to as the flow path. In accordance with the invention, structural features of the microscopic particles are determined either by light scattered from the particles as they pass through the fringes or by fluorescence induced by the fringes as the particles pass through them. The latter method is preferred for determining structural features of chromosomes such as centromeric index, chromosome length, and the like.

In accordance with the invention, a substantial portion of the scatter intensity and/or fluorescent intensity record of each particle, produced as it passes through the fringes, is stored and analyzed to extract structural information. This intensity record, accumulated as a particle passes through the fringes, will be referred to as the fringe profile. A crucial feature of the invention is the use of a data analysis algorithm to extract desired structural information from the fringe profile of a particle, or from the fringe profiles of a population of particles. The amount of structural information obtainable from a fringe profile depends critically on the light intensity pattern created by the one or more sets of interference fringes along the flow path. This pattern will be referred to as the fringe intensity pattern. Roughly, the greater the number of fringe sets with different interfringe distances, the greater the amount of information potentially available. Multiple and distinct interfringe distances within a fringe intensity pattern are obtained either by providing multiple fringe sets produced by pairs of laser beams converging at different angles, or by providing a single fringe set produced by converging more than two coplanar laser beams.

As a particle passes through the fringe intensity pattern its structure is "convolved" with structure of the fringe intensity pattern. That is, the fringe profile is the convolution of the particle structure with the fringe intensity pattern. As such, the useful information it contains about particle structure is not directly available. The data analysis algorithm "deconvolves" fringe profiles to obtain useful information on particle structure. The preferred method of deconvolving, or extracting, structural information from the fringe profile is by Wiener filtering.

The present invention is addressed to problems associated with determining the structure or morphology of microscopic particles, particularly chromosomes. It advantageously overcomes many of these problems by combining (1) flow system technology, which allows rapid analysis of large numbers of particles; (2) interference fringe illumination, which provides high resolution without depth-of-focus limitations; and (3) a data analysis algorithm, which extracts useful structural information from signals that otherwise have only limited utility (for example, assessing whether particle structure or morphology is uniform or not). In particular, the invention provides nearly an order of magnitude improvement in the resolution of chromosome structure over currently available flow-systems, allowing accurate and rapid determination of centromeric index, length, and DNA content of large numbers of chromosomes.

BRIEF DESCRIPTION OF THE DRAWINGS

The accompanying drawings, which are incorporated and form a part of the specification, illustrate an embodiment of the invention and, together with the description, serve to explain the principles of the invention.

DETAILED DESCRIPTION OF THE INVENTION

Reference will now be made in detail to the present embodiment of the invention, examples of which are illustrated in the accompanying drawings.

In accordance with the present invention a method and apparatus are provided for analyzing the morphology or structure of microscopic particles suspended in a carrier fluid. Microscopic particles are constrained to move along a flow path which passes perpendicularly through a set of interference fringes having a predetermined fringe intensity pattern. The particles fluoresce and/or scatter light as they pass through the set of interference fringes, generating a fringe profile containing structural and/or morphological information. The information is extracted by a data analysis algorithm.

Figure 1:
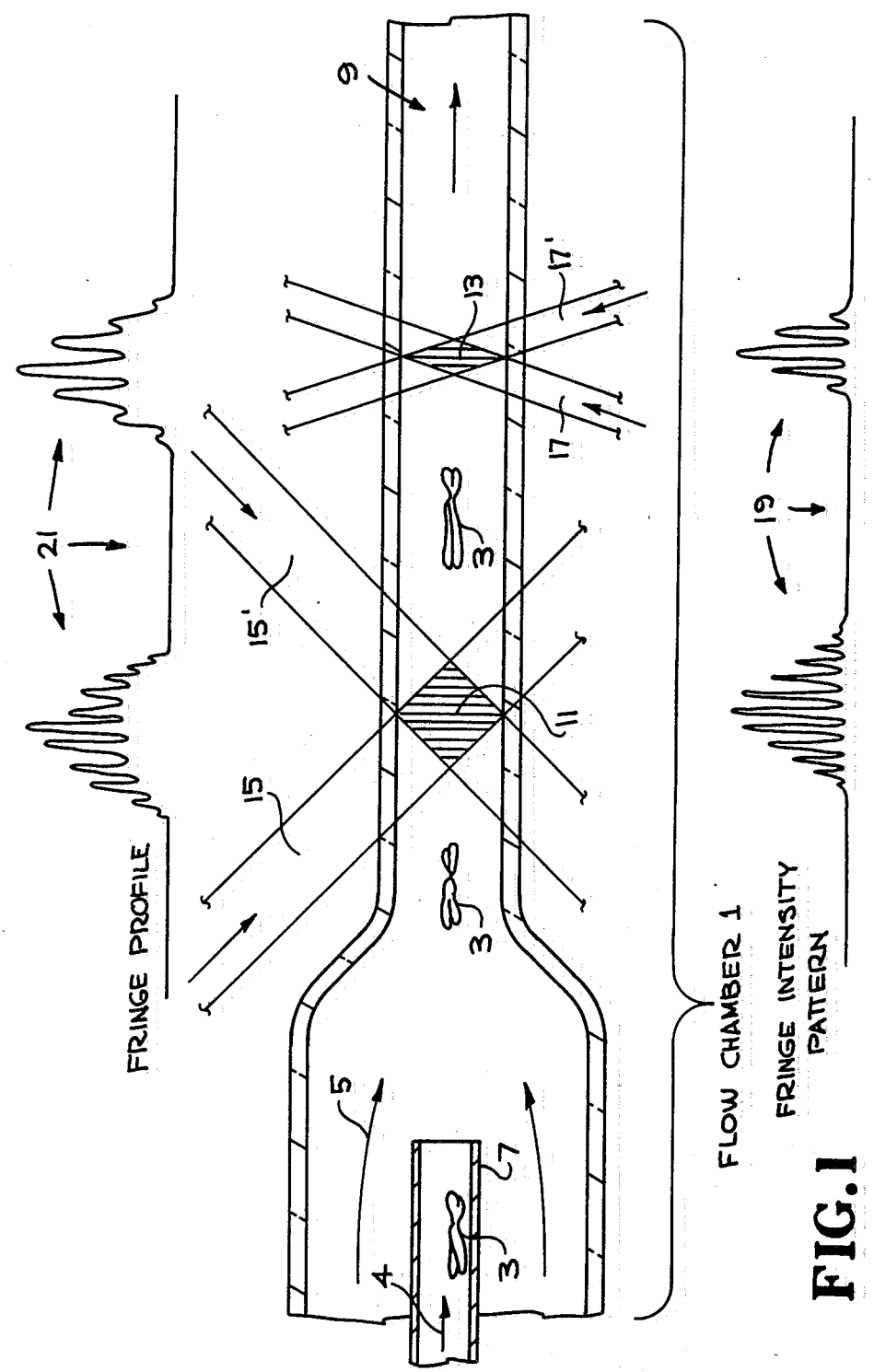
FIG. 1 illustrates a flow chamber suitable for constraining particles to flow sequentially along the same substantially linear path, and illustrates a fringe intensity pattern and a fringe profile for a dual two-beam-generated fringe embodiment.

By way of illustration the general operation of one embodiment of the invention is shown diagrammatically in FIG. 1. In a flow chamber 1 particles 3 (chromosomes in this case) suspended in a carrier fluid 4 are injected into a laminar stream of sheath fluid 5 by sample injection tube 7. Preferably, the microscopic particles should be suspended in a dispersed state without clumping in the carrier fluid at a density such that no more than one particle at a time is illuminated by the fringe intensity pattern. The sheath fluid and carrier fluid maintain laminar flow through the necked down portion of the flow chamber. The relative pressure of the sheath and carrier fluids is adjusted so that the diameter of the carrier fluid stream through the necked-down portion of the flow chamber is comparable to or less than that of the particles. (In the case of oblong particles, such as chromosomes, the diameter of the sample stream is narrowed to or below the narrow dimension of the particle.) As a result the particles are entrained to move sequentially along the substantially linear flow path 9, and oblong particles are oriented such that their longitudinal axes are parallel to the flow path. The entrained particles pass through one or more sets of interference fringes, oriented substantially perpendicular to the flow path. In FIG. 1 a first fringe set 11 and a second fringe set 13 are shown. The first fringe set 11 is generated by converging beams 15 and 15', and the second fringe set 13, having fringes with a different interfringe distance than the first fringe set, is generated by converging beams 17 and 17'. Such an arrangement produces a fringe intensity pattern akin to that illustrated by curve 19 in FIG. 1. As particles move through the fringe sets they produce scattered light and/or fluorescent light in response to the impinging light from the fringes. The temporal record of the intensity of light scattered or fluoresced is the fringe profile of the particle. For the two-fringe embodiment of the invention, a fringe profile is generated akin to that illustrated by curve 21 in FIG. 1. A unique feature of the invention is combining apparatus or steps for rapidly obtaining fringe profiles with a data analysis means or step for extracting desired structural information from the fringe profiles.

A data analysis means is required because particles are illuminated by multiple fringes. As each particle passes through a fringe set it is simultaneously illuminated by a plurality of fringes, each impinging on the particle at a different location. As a result, each point of the fringe profile is a sum of intensity contributions from each of the different locations. The object of the data analysis means is to estimate the structure of a particle (e.g. DNA distribution along a chromosome) given its fringe profile, a record of sums of intensity contributions from different regions of the particle, and a knowledge of the fringe intensity pattern. This objective can be attained in several ways (Deutsh, *Estimation Theory*, Prentice-Hall, Inc., Englewood Cliffs (1965) provides a review of several techniques which can be implemented for extracting structural information from the fringe profile data. Accordingly, this text is incorporated by reference as a guide to possible embodiments of the data analysis means; however, it is not intended that the invention be limited by the particular methods of analysis discussed in the text). The preferred data analysis means for determining the distribution of DNA along a chromosome employs a Wiener filter. In the absence of instrumental noise a chromosome DNA distribution could be determined from a fringe profile by straight forward Fourier analysis techniques. The fringe profile is the mathematical convolution of the chromosome DNA distribution and the fringe intensity pattern. The shape of the fringe intensity pattern is predetermined by the wavelength(s) of the laser beams and the angle(s) of their convergence, and the fringe profile is a measured quantity. If the fringe profile is modelled by a function for which a Fourier transform exists, then the chromosome DNA distribution can be determined by first dividing the Fourier transform of the fringe profile by the Fourier transform of the fringe intensity pattern, and then taking the inverse Fourier transform of the resulting function. This relation turns out to be unworkable in practice since the resulting function diverges whenever the Fourier transform of the fringe intensity pattern goes to zero, unless the Fourier transform of the fringe profile goes to zero at the same rate. This usually does not occur since the Fourier transform of the fringe profile has a noise component associated with the measurement process which makes it non-zero. The divergence problem can be avoided by using a Wiener filter as an approximation to the Fourier transform of the fringe intensity pattern. Constructing Wiener filters for the type of analysis just described is well known in the art of signal processing (e.g., Norgren, et al., "Restoration of Profiles from Slit-scan Flow Cytometry", IEEE Transactions on Biomedical Engineering, Vol. 29, pp. 101-106 [1982]). Fourier transforms and their inverses are computed with readily available fast fourier transform algorithms. In the implementation of the Weiner filter an estimate for the power density spectrum of the instrumental noise is required. A "white" noise approximation for the power density spectrum has produced suitable results. The magnitude of the "white" noise depends, of course, on the particular equipment used in constructing the invention. For example, it was found that water-cooled lasers generated greater noise because of vibrations caused by turbulance in the coolant passing through the laser.

In principle, the fringe intensity pattern, e.g., in the two beam case, can be determined by knowledge of the convergence angle of the beams and by knowledge of the beam profiles and intensities. In practice, the predicted pattern does not always correspond well with the actual pattern because of imperfect alignment of optics and so on. The fringe intensity profile can be determined experimentally by at least two methods. First, very small microspheres (e.g., 0.25 μm diameter or less) can be run through the system so that a scattered light signal is generated which is proportional to the fringe intensity pattern. Alternatively, the fringe intensity pattern can be determined by generating fringe profiles by running many larger diameter microspheres (e.g., 1.2 μm diameter) through the system and by reconstructing the fringe intensity pattern according to the method for estimating beam profiles in Norgren, et al., "Restoration of Profiles from Slit-scan Flow Cytometry", IEEE Transactions on Biomedical Engineering, Vol. 29, pp. 101–106 (1982). By this method particles of known shape, i.e., the microspheres, are passed through the fringe intensity pattern. The fringe intensity pattern is deduced by "deconvolving" the resultant signal (fringe profile) using a Wiener filter approximation for the microsphere.

Figure 2:
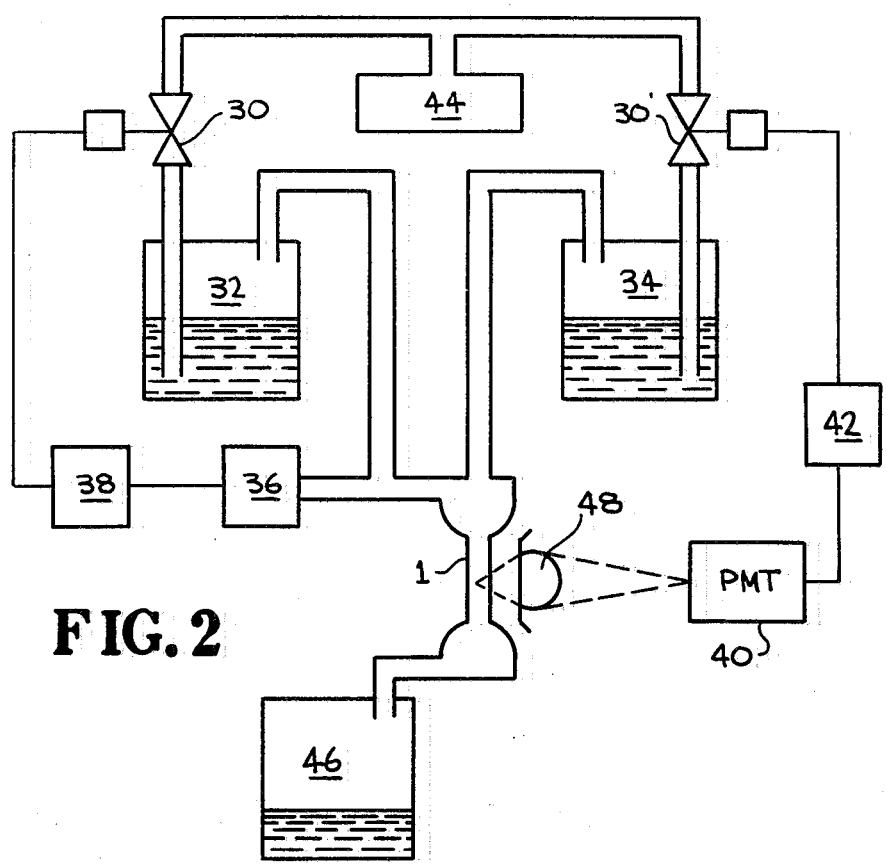
FIG. 2 illustrates a preferred embodiment of a fluidic control means.

Fluid control means suitable for use with the present invention are well known in the art (e.g., Fulwyler, et al., U.S. Pat. No. 3,710,933, issued Jan. 16, 1973; and Super, "The Ortho Cytogluorograf," Chapter 36 in Melamed, et al., *Flow Cytometry and Sorting*, John Wiley and Sons, New York). FIG. 2 diagrammatically illustrates one possible fluid control means for maintaining the carrier fluid stream diameter at a predetermined value in the region of the flow chamber where fringes are generated. Externally controlled pressure regulators 30 and 30' maintain pressure on both the sheath fluid reservoir 32 and the carrier fluid reservoir 34, respectively. The sheath fluid pressure is monitored at the flow chamber 1 by pressure transducer 36, and is regulated by controller 38 to maintain constant chamber pressure. The fluorescence resulting from the excitation of fluorescent dye in the carrier fluid stream (assumed to be proportional to carrier fluid stream diameter) is monitored by photomultiplier 40 (by way of lens 48). The pressure on the carrier fluid reservoir is regulated by controller 42 so that constant fluorescent intensity (and hence constant carrier fluid stream diameter) is maintained. Pressure regulators 30 and 30' operate off the same pressure reservoir 44, and fluids exiting the flow chamber are discarded into waste container 46. Feedback control of the fluid pressures is not a crucial feature of the present invention.

Figure 3:
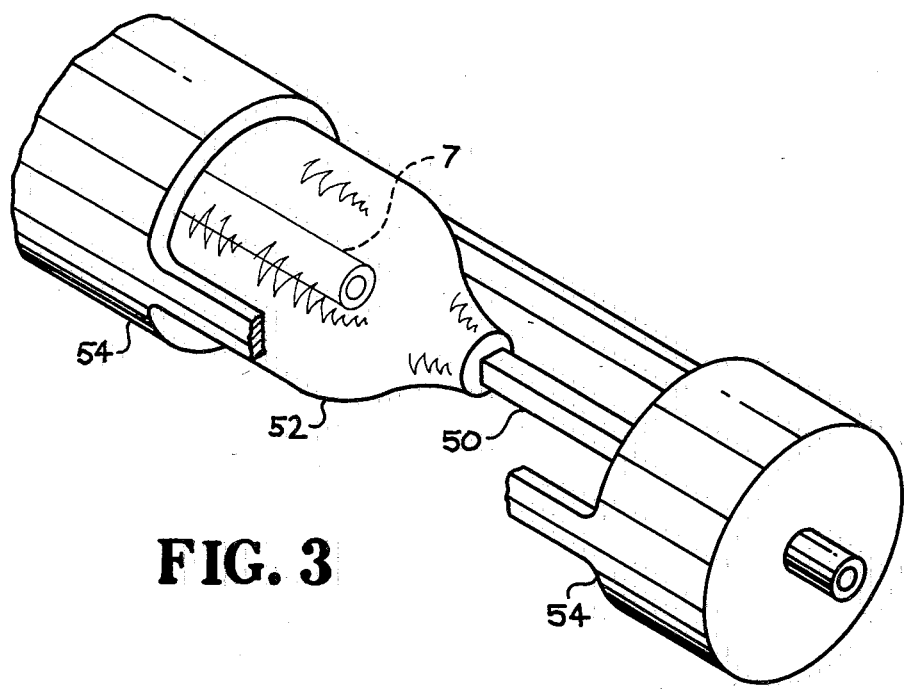
FIG. 3 illustrates a preferred flow chamber.

The design and application of flow chambers is also well known in the art (e.g., Eisert, U.S. Pat. No. 4,110,043, issued Aug. 29, 1978; and Hiebert, "Light Sources, Detectors, and Flow Chambers," Chapter 35 in Malamed, et al., *Flow Cytometry and Sorting*, John Wieley and Sons, New York). A preferred flow chamber for the fluid control means is illustrated in FIG. 3. The flow chamber comprises a glass capillary 50 with square cross-section inside and out (inside diameter 200 μm × 200 μm) glued into a drawn glass nozzle 52 of circular cross-section. The sample injection tube 7 has a 250 μm inside diameter and is disposed coaxially to the glass nozzle. The square-cross-section capillary is approximately 2 mm in length. The glass nozzle and square-cross-section capillary are mounted in brass housing 54. The housing, in turn, is mounted on mechanical positioners, not shown in FIG. 3. The use of this particular flow chamber is not crucial to the invention.

Figure 4:
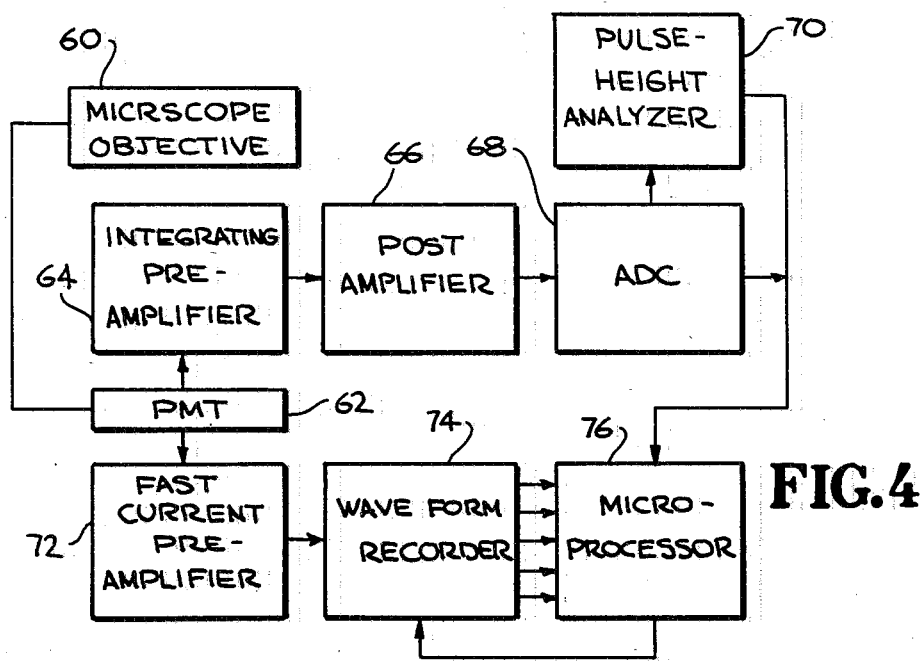
FIG. 4 illustrates a preferred embodiment of a detection means.

The step and means for detecting fringe profiles of chromosomes are subject to several embodiments. A preferred embodiment is illustrated diagrammatically in FIG. 4. Fluorescence from an illuminated chromosome is picked up by microscope objective 60 and focused on photomultiplier 62 (e.g., EMI model 9558B, EMI Electron Tubes, Middlesex, England) where it is converted to an electrical pulse. The signal from the last dynode of photomultiplier 62 is coupled to an integrating preamplifier 64 and post amplifier 66, the output of which is a voltage pulse proportional in height to the total chromosomal fluorescence. Each pulse is digitized by an analog-to-digital converter 68 and stored in the memory of a pulse height analyzer 70. The anode of the photomultiplier is coupled to a fast (e.g., 10 nsec response time) current preamplifier 72 which produces a voltage proportional to the instantaneous fluorescence from the chromosome being illuminated (The anode current can also be used to control the diameter of the carrier fluid stream). Each fast pulse from the anode, whose variation with time is proportional to the sum of fluorescence intensity contributions induced by fringe illumination, is digitized at 10 nsec intervals and stored in the memory of a waveform recorder 74 (e.g., Biomation model 8100, Gould, Inc., Santa Clara, CA). The waveform recorder is controlled by a microprocessor 76 (for example, a DEC LSI-11, Digital Equipment Corporation, Waltham, MA) to which recorded fringe profiles can be transferred for permanent storage and ultimately for processing by the data analysis means.

Additional embodiments of the detection means are possible depending on the type of particle that is being examined. The essential feature of all such embodiments is that fringe profiles be recorded or made available for processing by the data analysis means.

In accordance with the invention, fringe intensity patterns can be generated in several ways. For example, fringe intensity patterns are generated by converging one or more pairs of laser beams (i.e., each pair consists of two sub-beams from the same laser source) to form a sequence of fringe sets with different interfringe distances. Fringe intensity patterns are also generated by converging three or more coplanar laser beams (again from the same laser source) at a common point. That is, a single laser beam is split into three or more coplanar, and preferably equal intensity, sub-beams which are converged to a common point adjacent to the flow path such that interference fringes are formed that intersect and are substantially perpendicular to the flow path. As with the case where pairs of beams are converged to generate fringe intensity patterns, more than one three-or-more-sub-beam fringes may be employed. Preferably, the angles of convergence between the sub-beams from the same laser beam are different. That is, preferably the relative angles, or the angles between adjacent converging sub-beams, are different. Fringe sets created by converging three or more sub-beams have more complicated structures than fringe sets created by converging two sub-beams. For example, converging three coplanar beams produces a fringe set with two different interfringe distances; thus, the corresponding fringe profiles contain more information on particle structure than than those produced by two-beam-generated fringe sets.

Preferably the converging beams have equal intensity; otherwise the intensity contrast between fringe peaks and troughs within a fringe set is decreased. Fringe intensity can be increased by overlapping two sets of fringes generated by different lasers. Here the wavelengths and beam-convergence angles must be chosen so that the interfringe distances of the overlapping fringe sets are substantially the same.

The preferred fringe intensity pattern is a sequence of two-beam-generated fringe sets with different interfringe distances. The distance between the fringe sets is not critical insofar as the data analysis means are concerned (short of overlapping which substantially destroys the contrast between fringe peaks and troughs). However, preferably the fringe sets should be spaced closely together, e.g., contiguous but not substantially overlapping, since particles can change orientation while traveling along the flow path. Such changes in orientation can give rise to spurious fringe profiles.

Figure 6:
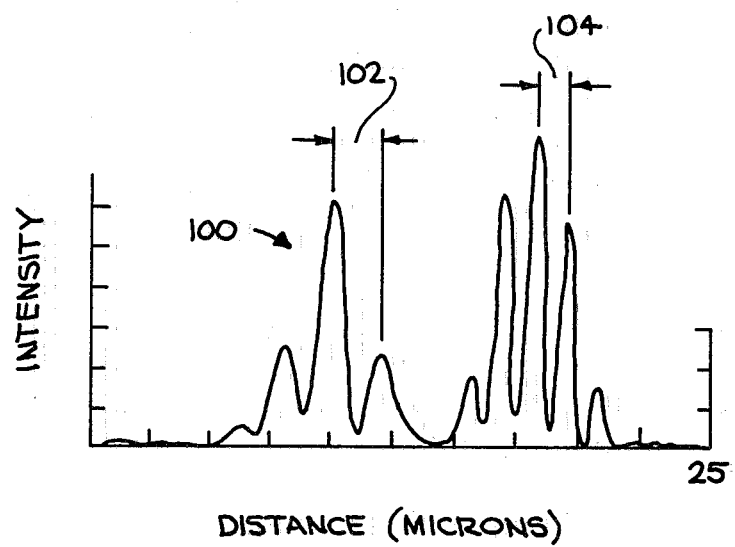
FIG. 6 shows a curve representing a fringe intensity pattern comprising two fringe sets with different interfringe distances.
Figure 5:
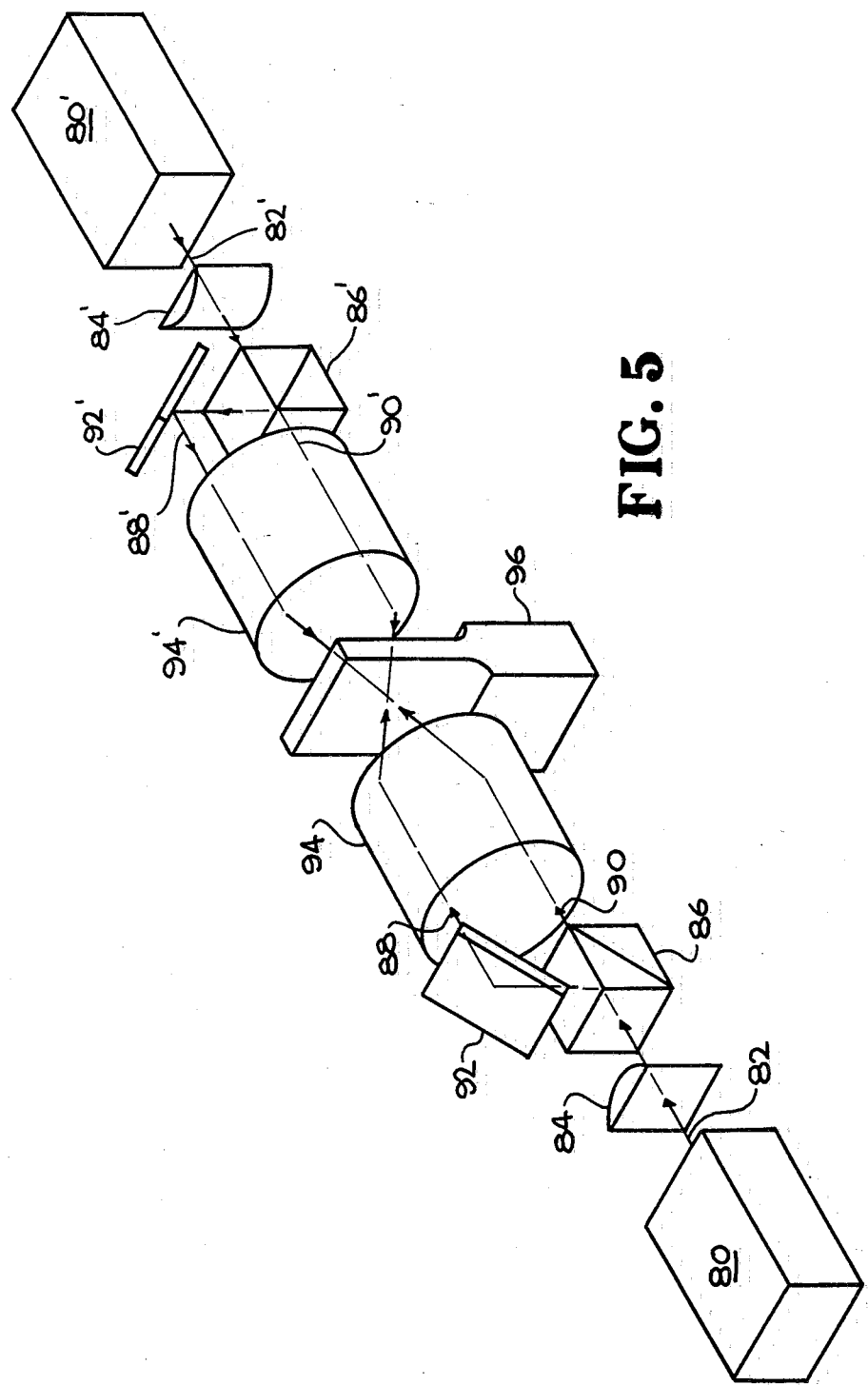
FIG. 5 illustrates a preferred embodiment of a means for generating a two-fringe fringe intensity pattern.

FIG. 5 illustrates an embodiment of a means for generating perferred fringe intensity patterns. Lasers 80 and 80' each generate laser beams 82 and 82', respectively. (For example, for analysis of chromosomes stained with the fluorescent dye, ethidium bromide, 80 and 80' can be argon-ion lasers, e.g., Spectra Physics, Mountain View, CA, model 164, tuned to lase at 488 nm or 514 nm). Each beam passes through a cylindrical lens, 84 and 84', respectively for producing a flattened, or elliptical, beam profile. The cylindrical lens is arranged so that the longitudinal axis of the beam profile is coplanar with the subsequently converged beams, 88 and 90 for cylindrical lens 84, and 88' and 90' for cylindrical lens 84'. The flattened beams are then split: 82 by beam splitter 86, and 82' by beam splitter 86', to form two pairs of equi-intensity beams, the pairs comprising a first beam, 88 and 88' from lasers 80 and 80', respectively, and a second beam, 90 and 90' from lasers 80 and 80', respectively. First beams, 88 and 88', are deflected by mirrors 92 and 92', respectively, so that they leave the mirrors parallel to beams 90 and 90', respectively. The first and second beams next enter microscope objectives, 94 for 88 and 90, and 94' for 88' and 90'. The microscope objectives determine the angles at which the respective beam pairs are converged at the flow path within flow chamber 96. Beams 88 and 90, spaced approximately 20 m apart, entering microscope objective 94 and beams 88' and 90', similarly spaced, entering microscope objective 94' produce fringe intensity pattern 100 as shown in FIG. 6. Beams 88 and 90 produce a fringe set along the flow path with interfringe distance 102 of approximately 1.9 μm and beams 88' and 90' produce a fringe set along the flow path with interfringe distance 104 of approximately 1.3 μm. For this embodiment, interfringe distance is related to convergence angle by the following formula:

$$d = \lambda/[2.66 \sin(\theta/2)]$$

where d is the interfringe distance, λ is the wavelength, and θ is the convergence angle.

Preparing particles for fringe scanning depends, of course, on the nature of the particle. The only fundamental requirement is that particles be suspended in a fluid, preferably in a dispersed state without clumping, so that they may be constrained to flow sequentially along a flow path by the fluidic control means. For biological particles, such as chromosomes, staining with one or more fluorescent dyes is preferred. Obtaining isolated chromosome suspensions suitable for use with the present invention is known in the art. Accordingly, Carrano, et al., Flow Cytogenetics: A New Approach to Chromosome Analysis, Chapter 23 in Melamed, et al., *Flow Cytometry and Sorting*, John Wiley and Sons, New York, is incorporated by reference as a source of examples for chromosome preparation and staining suitable for use in accordance with the present invention.

The descriptions of the foregoing embodiments of the invention have been presented for purposes of illustration and description. They are not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

We claim:

1. A method for determining the longitudinal morphology of oblong microscopic particles, each oblong microscopic particle having a longitudinal axis, the method comprising the steps of:
   (a) suspending the oblong microscopic particles in a carrier fluid;
   (b) constraining the oblong microscopic particles to sequentially flow along a flow path which is substantially the same for every oblong microscopic particle and in which the longitudinal axis of each oblong microscopic particle is oriented to be substantially parallel to the flow path;
   (c) generating a fringe intensity pattern, the fringe intensity pattern having a plurality of fringes, each being disposed substantially perpendicularly to the flow path;
   (d) detecting and recording a fringe profile as an oblong microscopic particle passes through the fringe intensity pattern; and
   (e) deconvolving the fringe intensity pattern from the fringe profile to obtain information about the longitudinal morphology of the oblong microscopic particle.

2. The method as recited in claim 1, wherein said step of generating a fringe intensity pattern includes:
   (a) splitting each of a plurality of laser beams to form pairs of distinct beams, each pair comprising a first beam and a second beam, the first beam and the second beam having substantially the same intensities; and
   (b) converging the first beam and second beam of each pair of distinct beams to form a sequence of sets of interference fringes arranged such that each set of interference fringes intersects the flow path and that each fringe within each set of interference fringes is substantially perpendicular to the flow path.

3. The method as recited in claim 2, wherein said step of converging includes choosing different angles of convergence for each said first beam and said second beam of each said pair of distinct beams such that sets of interference fringes with different interfringe distances are generated.

4. The method as recited in claim 1 wherein, in the case where said oblong microscopic particles are chromosomes, said step of suspending includes staining the chromosomes with one or more fluorescent dyes.

5. The method as recited in claim 1, wherein said step of generating said fringe intensity pattern includes:
   (a) splitting a laser beam into a plurality of separate coplanar beams, the separate coplanar beams each having substantially the same intensity; and
   (b) converging the separate coplanar beams at a common point adjacent to said flow path such that a set of interference fringes is generated which intersects said flow path and whose fringes are substantially perpendicular to said flow path.

6. The method as recited in claim 1 wherein said step of deconvolving includes constructing a Wiener filter for said fringe intensity pattern.

7. Apparatus for determining the longitudinal morphology of oblong microscopic particles, each oblong microscopic particle having a longitudinal axis, the apparatus comprising:
   (a) fluidic control means for constraining oblong microscopic particles suspended in a carrier fluid to flow sequentially along substantially the same flow path such that the longitudinal axis of each oblong microscopic particle is oriented to be substantially parallel to the flow path;
   (b) fringe generation means for producing a fringe intensity pattern adjacent to the flow path such that the fringes of the fringe intensity pattern intersect the flow path and are substantially perpendicular to the flow path;
   (c) detection means for detecting and recording fringe profiles for each oblong microscopic particle as it passes through the fringe intensity pattern; and
   (d) data analysis means for deconvolving the fringe intensity pattern from the fringe profile to obtain information about the longitudinal morphology of the oblong microscopic particle.

8. The apparatus as recited in claim 7 wherein said fringe generation means comprises one or more laser beams generated by different lasers, each laser beam being split into a first beam and a second beam, the first beam and the second beam of each laser beam having substantially the same intensity, and the first beam and the second beam of each laser beam being converged to a point adjacent to said flow path such that a set of interference fringes are generated whose fringes intersect said flow path and are substantially perpendicular to said flow path.

9. The apparatus as recited in claim 8 wherein said one or more laser beams includes two laser beams.

10. The apparatus as recited in claim 7 wherein said fringe generation means comprises one or more laser beams generated by different lasers, each laser beam being split into three or more coplanar sub-beams, each sub-beam having substantially the same intensity as every other sub-beam from the same laser beam, and each sub-beam from the same laser beam being converged at different relative angles to a common point adjacent to said flow path such that interference fringes are formed, the interference fringes being substantially perpendicular to and intersecting said flow path.

11. A method for flow karyotyping chromosomes, the method comprising the steps of:
   (a) staining the chromosomes with one or more fluorescent dyes;
   (b) suspending the chromosomes in a carrier fluid;
   (c) constraining the chromosomes to sequentially flow along substantially the same flow path such that the longitudinal axis of each chromosome is substantially parallel to the flow path;
   (d) generating a fringe intensity pattern, the fringe intensity pattern having a plurality of fringes each intersecting the flow path and each being disposed substantially perpendicular to the flow path;
   (e) detecting and recording a fringe profile as each chromosome passes through the fringe intensity pattern; and
   (f) deconvolving chromosome structure from the fringe profile and the fringe intensity pattern.

12. The method as recited in claim 11 wherein said step of staining includes staining with a DNA-specific fluorescent dye.

13. The method as recited in claim 11 wherein said step of deconvolving chromosome structure includes constructing a Wiener filter of said fringe intensity pattern.

14. The method as recited in claim 11 wherein said step of deconvolving chromosome structure includes calculating chromosome length and centromeric index.

* * * * *